(12) United States Patent
Figueredo

(10) Patent No.: US 9,445,598 B2
(45) Date of Patent: Sep. 20, 2016

(54) BIOCIDE COMPOSITIONS COMPRISING QUATERNARY AMMONIUM AND UREA AND METHODS FOR THEIR USE

(71) Applicant: United Promotions, Inc., Atlanta, GA (US)

(72) Inventor: Fernando Figueredo, Atlanta, GA (US)

(73) Assignee: United Promotions, Inc., Atlanta, GA (US)

( * ) Notice: Subject to any disclaimer, the term of this patent is extended or adjusted under 35 U.S.C. 154(b) by 18 days.

(21) Appl. No.: 13/690,468

(22) Filed: Nov. 30, 2012

(65) Prior Publication Data

US 2013/0225456 A1  Aug. 29, 2013

Related U.S. Application Data

(63) Continuation of application No. 12/418,793, filed on Apr. 6, 2009, now abandoned.

(60) Provisional application No. 61/061,266, filed on Jun. 13, 2008.

(51) Int. Cl.
| | |
|---|---|
| A01N 47/28 | (2006.01) |
| A01N 33/12 | (2006.01) |
| C09K 8/035 | (2006.01) |

(52) U.S. Cl.
CPC .............. *A01N 47/28* (2013.01); *A01N 33/12* (2013.01); *C09K 8/035* (2013.01)

(58) Field of Classification Search
None
See application file for complete search history.

(56) References Cited

U.S. PATENT DOCUMENTS

| | | | |
|---|---|---|---|
| 2,676,955 A | | 4/1954 | Weitkamp et al. |
| 2,700,683 A | * | 1/1955 | Tesoro et al. ................. 564/282 |
| 2,957,187 A | | 9/1960 | Lo Cicero |
| 2,957,188 A | | 10/1960 | Bingham |
| 4,336,165 A | * | 6/1982 | Weisensel ..................... 510/278 |
| 5,044,093 A | * | 9/1991 | Itoh et al. ........................ 34/585 |
| 5,324,649 A | | 6/1994 | Arnold et al. |
| 5,650,446 A | | 7/1997 | Wellinghoff et al. |
| 6,028,113 A | | 2/2000 | Scepanski |
| 6,277,311 B1 | * | 8/2001 | Eimer ................... C07C 273/02 264/117 |
| 7,007,338 B2 | | 3/2006 | Garabedian, Jr. et al. |
| 7,589,054 B2 | | 9/2009 | Ohlhausen et al. |
| 2003/0152610 A1 | | 8/2003 | Rolf et al. |
| 2004/0071757 A1 | | 4/2004 | Rolf |
| 2004/0091448 A1 | | 5/2004 | Kross |
| 2006/0093675 A1 | | 5/2006 | Ebmeier et al. |

FOREIGN PATENT DOCUMENTS

| | | |
|---|---|---|
| DE | 19781549 B4 | 5/2005 |
| EP | 1411776 A1 | 4/2004 |
| EP | 1942112 A1 | 7/2008 |
| GB | 1440875 A | 6/1976 |
| GB | 2171013 A | 8/1986 |
| JP | 60087246 A * | 5/1985 ............ C07C 87/30 |
| JP | 2006111605 A | 4/2006 |
| WO | 9214362 A1 | 9/1992 |
| WO | 9518212 A1 | 7/1995 |
| WO | 9960081 A1 | 11/1999 |
| WO | 9960082 A1 | 11/1999 |
| WO | 2004037225 A2 | 5/2004 |
| WO | 2005102046 A1 | 11/2005 |
| WO | 2006005108 A1 | 1/2006 |

OTHER PUBLICATIONS

PCT/US2009/047042 International Search Report and Written Opinion mailed Aug. 27, 2012.
Cox et al., Bactericidal effect of several chemicals on hatching eggs inoculated with *Salmonella serovar* Typhimurium, Journal of Applied Poultry Research (2007), 16(4), 623-627 CODEN: JAPRFS; ISSN: 1056-6171.
Cutter et al., Application of Carnatrol and Timsen to decontaminate beef, Journal of food protection, Dec. 1996. vol. 59, No. 12. p. 1339-1342 Publisher: Des Moines, Iowa : International Association of Milk, Food and Environmental Sanitarians. CODEN: JFPRDR; ISSN: 0362-028X.
Saad et al., Flow injection potentiometric determination of paraquat in formulations and biological samples,Talanta : (Oxford), (1998), 47(5), 1231-1236, 13 refs. ISSN: 0039-9140 CODEN: TLNTA2.
Minarik et al., The effect of some surface active substances on yeasts occurring on secondary habitats in wineries, Yeasts, Models Sci. Tech., Proc. Spec. Int. Symp., 1st (1972), Meeting Date 1971, 417-30. Editor(s): Kockova-Kratochvilova, Anna; Minarik, Erich. Publisher: Publ. House Slovak Acad. Sci., Bratislava, Czech. CODEN: 32HTAD.
Jochen Oertel, Novel wood preservatives of good leaching resistance, based on organic compounds soluble in water, and their potential uses, Holztechnologie (1965), 6(4), 243-7 CODEN: HLZTAW; ISSN: 0018-3881.
Gismondo et al., Antimicrobial and sporicidal efficacy of various disinfectant solutions, Efficacia antimicrobica e sporicida di varie soluzioni disinfettanti, Minerva medica, (Jan.-Feb. 1995) vol. 86, No. 1-2, pp. 21-32. Journal code: 0400732. ISSN: 0026-4806. In Italian.
Cadwallader et al., Urea as a Tableting Agent for Benzakonium Chloride, Journal of Pharmaceutical Sciences, Technical Articles, vol. 58, No. 2, Feb. 1969, pp. 239-241.
Robert R. Rafael R., Identification and Control of Foliar Spot Pathogen in Tagetes erecta L., National Agricultural University La Molina Phytopatology Specialty, Lima, Peru, Seminar II Dec. 12, 2000.

(Continued)

*Primary Examiner* — Kyle Purdy
(74) *Attorney, Agent, or Firm* — James P. Muraff; Neal, Gerber & Eisenberg LLP

(57) ABSTRACT

Composition and method for treating and/or preventing biological contamination using a biocide composition comprising at least one quaternary ammonium compound and urea. The method includes drying urea, and thereafter combining at least one quaternary ammonium compound and urea and may produce a potent biocide composition that is stable and able to chemically treat biological contamination in a variety of difficult to reach locations. Uses of the composition are also described.

8 Claims, No Drawings

(56) References Cited

OTHER PUBLICATIONS

Russell, S. M., Chemical Sanitizing Agents and Spoilage Bacteria on Fresh Broiler Carcasses, Applied Poultry Science, Inc., 1998 J. Appl. Poultry Res. vol. 7, pp. 273-280.
Protocol of Application of Prontech and CT-500 Hands in McDonald's—Colombia, Promotoras Unidas Ltda., Technical Department Promotoras Unidas Ltda., www.upitrading.com Bogota, Nov. 2007.
Russell, Scott, Scalding, picking a big opportunity?, Poultry USA Magazine, May 7, 2007, 10 pages.
Krog et al., Alkyl-Dimethyl-Benzyl-Ammonium-Chloride for Sanitization of Eating and Drinking Utensils, American Journal of Public Health, Apr. 1940, pp. 341-348.
Russell S. M., Effect of a Novel Sanitizer on Pathogenic, Spoilage, and Indicator Populations of Bacteria from Chicken Carcasses, 2000 J. App. Poultry Res. vol. 9, pp. 393-402.
Williams, Sally K., The Poultry Food System: A Farm to Table Model, 2006 Regional Project Progress Report European Poultry Conference Verona, Italy, Sep. 9, 2006, 3 pages.
PRONTECH, Newsletter, vol. 1, Jan. 2007, 2 pages.
International Redes Del Mar Article titled "Nuevos desafios en la Ingenieria Naval Ecuatoriana", dated Dec. 2004, 8 pages.
Tlmsen Article titled "University of George Department of Poultry Science", dated Aug. 2006, 2 pages.
Article titled "Nueva tecnologia", dated Apr. 9, 2000, 1 page.
Nuovo El Diario Article titled "Ferquido presenta fungicida controla hongos y bacterias" dated Sep. 4, 2000, 1 page.
El Nacional Article titled "Ferquido presenta nuevo fungicida" dated Mar. 9, 2000, 1 page.
German Timsen Article titled "TIMSEN", 8 pages.
Timsen Chart titled "Timsen Programa HACCP de Sanitizacion en Plantas de Proceso de Melon",v 2 pages.
Label page titled "TRIGGER", 1 page.
Label page titled "TIMSEN", 1 page.
Label page titled "Aquaculture TIMSEN", 1 page.
Article for Directions titled "TIMSEN in Fish Processing Plant", 2 pages.
Timsen Article titled "Aquaculture Timsen", 2 pages.
Timsen Ads for Poultry, 7 pages.
Timsen Floriculture Labels titled "For Today's Market and Tomorrow's World" 2 pages.
Timsen Article from Hangzhou Advansafe Biotech Co., Ltd., 10 pages.
Instructions for using Nemasolve 618, 1 page.
Timsen Use Instructions titled "Para Uso en Hosptiales y Laboratorios", 4 pages.
CT-500 Instructions, 2 pages.
CT-500 Characteristics page, 4 pages.
Timsen Application and Uses Chart, 2 pages.
Timsen Article titled "Timsen . . . Actua a Fondo Y no Contamina", 4 pages.
Timsen Article titled "Flores Belles Con . . . Timsen", 5 pages.
Dorliagro Article from the Divison Agricole de Dorlia S.A., 26 pages.
Timsen article titled "Poultry Timsen" from United Promotions, Inc., 2 pages.
Timsen label in Greek, 1 page.
Timsen Labels and Instructions from AGR Team, 10 pages.
Timsen Label in Japanese from United Promotions Inc., 1 page.
Timsen Article titled "Protegiendo tu futuro", 10 pages.
Timsen letter to Sr. Fernando Figueredo from David Ulises Alvares, 3 pages.
Timsen Poultry Disinfectant Ads and Instructions, 4 pages.
Timsen Agroindustria Warning Label, 1 page.
Arabic Timsen Label, 1 page.
Timsen Article titled "Para el Mercado de frutos y vegetates" 2 pages.
Timsen Warning Label 40 WG, 1 page.
Timsen 40 WG Warning Label and Forms of Usage, 2 pages.
Timsen Use Label titled "Formulacion en granulos solubles", 2 pages.
Timsen Article titled "Para el Mercado de hoy y el Mundo del Mariana", 9 pages.
Timsen Ad titled "Solucion TOTAL en Desinfeccion", 2 pages.
Timsen Warning Label titled "Formulacion en granulos solubles", 3 pages.
Timsen Arabic Warning Label, 1 page.
Timsen Arabic Warning Label, 2 pages.
Porcicola Timsen Article title "Para el Mercado de Hoy y el Mundo de Mariana", 2 pages.
Timsen Article title "Uso de Timsen en Agua de Bebida y Nebulizacion Ambiental en el Polio de Engorda", dated Apr. To May 2003, 10 pages.
Timsen Article titled "Acuacultura del Equador" 3 pages.
Floral Enhancer Ad titled "Preservativo Para Floires Cortadas", 3 pages.
German Letters for Timsen, dated Oct. 23, 1989, 4 pages.
Timsen Ads in Hebrew, 3 pages.
Timsen Ad in Hebrew titled "The Optimum Biocide", 1 page.
Department of Pathology Experiment titled "Efficacy of Tlmsen against Experimental Gumboro Disease in Broilers", dated May 2004, 27 pages.
Letter to United Promotions Inc. from William E. Mims, dated Sep. 19, 1998, 2 pages.
Timsen Powerpoint Presentation titled "For Today's Market and Tomorrow's World", 10 pages.
MB Research Laboratories, Inc. Experiment for "Single Dose Oral Toxicity in rats/LD 50 in rats", 3 pages.
The University of Georgia Final Report on "Evaluation of the Sanitizer Timsen for use in Poultry Processing Waters", 7 pages.
PRONTECH: Advantages Solubility Powerpoint Presentation, 20 pages.
Timsen Research Summary Report 1997, Department of Plant Pathology, The Ohio State University, 2 pages.
Rossini, Lavinia, J.F. Laboratory for Animal Pathology SC Ltd. Brasil 2002, 3 pages.
Algaecide can decrease the growth of Lemna in Maracaibo Lake, Extracts of the paper published in Panorama Digital Venezuela, Oct. 26, 2004, 1 page.
NAIN—National Antimicrobial Information Network, List C: Products registered with the EPA which are labeled for use against HIV-1 (human immunodeficiency virus), Mar. 2001, 1 page.
La industria camaronera bajo el programa HACCP (Hazard Analysis and Critical Control Point), Internacional Redes Del Mar, Año 5 No. 16, Dec. 2004.
Acuacultura Del Ecuador, Acuacultura y Medio Ambiente, Revista, May-Jun. 1996, Guayaquil, Ecuador, vol. 15, newsletter, 9 pages.
Chowdbury, E. H., Management of Infectious Bursal Disease in Broilers Using Timsen (40% N-alkyl dimethyl benzyl ammonium chloride), Associate Professor, Department of Pathology, BAUm Mymensingh, 1 page.
Russell, S. M., Effect of a Novel Sanitizer on Pathogenic, Spoilage, and Indicator Populations of Bacteria from Chicken Carcasses, 2000 Journal Applied Poultry Res. vol. 9, pp. 393-402.
Russell, S. M., Chemical Sanitizing Agents and Spoilage Bacteria on Fresh Broiler Carcasses, 1998 Journal Applied Poultry Res. vol. 7, pp. 273-280.
Quat Test Kit Model QAC2-DC—Code 7057, 13 pages.
Taiwan IPO Search Report Invention Patent Application No. 098119211 dated Mar. 7, 2014.

* cited by examiner

BIOCIDE COMPOSITIONS COMPRISING QUATERNARY AMMONIUM AND UREA AND METHODS FOR THEIR USE

CROSS-RELATED APPLICATIONS

The present application is a continuation application which claims priority to U.S. patent application Ser. No. 12/418,793, filed on Apr. 6, 2009 and Provisional Application Ser. No. 61/061,266, filed on Jun. 13, 2008, the disclosures of which are incorporated herein by reference in their entirety.

TECHNICAL FIELD

The present application relates generally to biocide compositions, and more particularly relates to biocide compositions including quaternary ammonium and urea.

BACKGROUND OF THE INVENTION

Biological contamination by pathogens such as bacteria, fungus, algae and viruses may cause significant problems in a variety of products and processes. Unfortunately, the locations and conditions in which biological contamination occurs may create obstacles to treating the contamination. For example, contamination may occur (1) at temperatures at which traditional biocides are unstable; (2) in locations such as crevices, pockets, and pores that are too difficult to reach with traditional biocides; (3) in products such as a food that are not permitted to come in direct contact with traditional biocides; and (4) in the presence of organic matter that may destroy or breakdown the effectiveness of traditional biocides.

It would therefore be desirable to provide biocide compositions and methods of treating pathogens that overcome one or more of these limitations. The compositions and methods may be inexpensive, may require low levels of non-toxic biocide, may be stable and effective at high and low application temperatures, may have enhanced wetting properties, may provide effective treatment over a wide range of pH, and/or may provide effective treatment in a wide variety of products and processes.

SUMMARY OF THE INVENTION

The present application thus provides improved methods for preparing biocide compositions and improved methods for treating and/or preventing biological contamination using a biocide composition comprising at least one quaternary ammonium compound and urea. In accordance with an embodiment of this invention, it has now been discovered that drying urea, and thereafter combining at least one quaternary ammonium compound and urea may produce a potent biocide composition that is stable at high temperature and able to chemically treat biological contamination in a variety of difficult to reach locations. As used herein, stable means the biocide remains effective as a biocide with substantially the same potency as when first made and the biocide components do not substantially separate from one another.

DETAILED DESCRIPTION OF EMBODIMENTS

The Biocide Composition

The biocide compositions described herein are useful in treating and/or preventing many types of biological contamination. Non-limiting examples of contamination suitable for treating and/or treating include bacteria, fungus, algae and viruses. In an embodiment, the biocide composition may comprise urea and a quaternary ammonium compound. In another embodiment, the biocide composition may comprise urea and a plurality of quaternary ammonium compounds.

Urea has a chemical formula of $(NH_2)_2CO$. In an embodiment, the biocide composition comprises urea that is substantially free of impurities. In a particular embodiment, the biocide composition comprises urea that is pharmaceutical grade.

Quaternary ammonium compounds, also known as "quats," are alkyl dimethyl benzyl ammonium chlorides. Quats have a structure in which a nitrogen atom (N) is covalently bonded to two methyl groups ($CH_3$), one benzyl group ($CH_2C_6H_5$), and one alkyl chain (R) to form a positively charged cation that may be stabilized by a negatively charged chlorine (Cl) ion. According to an embodiment of the present invention, in a dry form, the biocide composition may be stabilized and non-ionic or neutral due to the association of the quat cation with the chlorine ion. When the biocide composition is diluted in water, the chlorine molecule may detach from the anion.

In a preferred embodiment, the quat has the following structure:

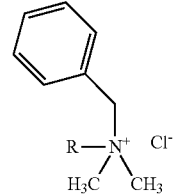

The alkyl chain (R) may have a length in the range of about eight carbons ($C_8H_{17}$) to about eighteen carbons ($C_{18}H_{37}$). Non-limiting examples of suitable alkyl chains include $C_8H_{17}$, $C_9H_{19}$, $C_{10}H_{21}$, $C_{11}H_{23}$, $C_{12}H_{25}$, $C_{13}H_{27}$, $C_{14}H_{29}$, $C_{15}H_{31}$, $C_{16}H_{33}$, $C_{17}H_{35}$, and $C_{18}H_{37}$. In a particular embodiment, the biocide composition comprises a quaternary ammonium compound in which the alkyl chains have a chain length that is substantially identical in each of the quat molecules. In another embodiment, the biocide composition comprises one or more quaternary ammonium compounds in which the length of the alkyl chain varies between the quat molecules.

In an embodiment of this invention, the quat/urea biocide composition comprises one or more quaternary ammonium compounds in which the alkyl chain has a length in the range of about 12 carbons to about 18 carbons. For example, according to an embodiment, about 50 to about 100% by weight of the one or more quaternary ammonium compounds present in the quat/urea biocide composition have an alkyl chain has a length in the range of about 12 carbons to about 18 carbons. According to another embodiment, about 50 to about 100% by weight of the one or more quaternary ammonium compounds present in the quat/urea biocide composition have an alkyl chain has a length in the range of about 14 carbons to about 16 carbons. Furthermore, according to a certain embodiment, 60% by weight of the one or more quaternary ammonium compounds present in the quat/urea biocide composition have a $C_{16}H_{33}$ alkyl chain, 30% by weight of the one or more quaternary ammonium compounds present in the quat/urea biocide composition have a $C_{14}H_{29}$ alkyl chain, 5% by weight of the one or more quaternary ammonium compounds present in the quat/urea biocide composition have a $C_{12}H_{25}$ alkyl chain, and 5% by weight of the one or more quaternary ammonium compounds present in the quat/urea biocide composition have a $C_{18}H_{37}$ alkyl chain.

Furthermore, according to certain embodiments of the present invention, the quat/urea biocide composition is substantially dry when made and while stored so that the quat/urea biocide composition remains stable and non-ionic or neutral due to the association of the quat cation with the chlorine ion. Thus, according to certain embodiments of the present invention, the quat/urea biocide composition comprises water in an amount no more than about 3% by weight of the quat/urea biocide composition, or no more than about 2% by weight of the quat/urea biocide composition, or no more than about 1% by weight of the quat/urea biocide composition. As will be explained in more detail below in the description of certain embodiments for making the biocide composition, the one or more quats and urea are dried before they are mixed together and the one or more quats and urea are combined in a manner and in a weight ratio so that the urea and the one or more quats may bind into a single product, the urea may become chelated, and/or the one or more quats may become encapsulated in the urea, the biocide composition may be stabilized and non-ionic or neutral due to the association of the quat cation with the chlorine ion, and the orientation of the biocide at interfaces may be substantially perfect so the biocide composition may impart a substantially reduced surface tension to water when added to water to form an aqueous solution. According to certain embodiments, the one or more quats and urea are present in the biocide composition in amounts based on a weight ratio of the one or more quats to urea from about 10:90 to about 90:10, or from about 20:80 to about 60:40, or from about 30:70 to about 50:50, or a weight ratio of about 40:60.

Method of Making the Biocide Composition

According to an embodiment of this invention, a method of making the biocide composition may comprise the steps of drying the urea and then combining the one or more quats and the urea to form a biocide composition. According to another embodiment of this invention, a method of making the biocide composition may comprise the steps of drying the one or more quats and urea and then combining the one or more quats and the urea to form a biocide composition. According to an embodiment, the method also may include removing solvent from the combined quat and urea composition and/or granulating the composition.

According to an embodiment, the step of drying the one or more quats and urea may include separately drying the one or more quats and urea. In a particular embodiment, the urea is heated to a temperature in a range from about 80 to about 120° C., or about 90 to about 110° C., or to a temperature of about 100° C., and, separately from the urea, the one or more quats are gradually heated to a temperature of up to about 50° C., or to a temperature from about 30 to about 40° C. Thus, according to an embodiment, the one or more quats may be heated over a period of about 30 to about 120 minutes while gradually increasing the temperature at a rate of about 0.2 to about 1.5° C. per minute. As a result of the gradual heating, the one or more quats may be substantially dried without affected the stability of the quat molecules.

According to a particular embodiment, the drying of quats may take place at a very low level of humidity. Alternatively, if humidity level is above about 10%, the drying treatment may take place after a step of adding organic solvent to the quats. In other words, an organic solvent may be added to the one or more quats before heating the one or more quats. According to particular embodiments, the organic solvent may include an alcohol, glycol, ketone, or combinations thereof. In a particular embodiment, the organic solvent comprises ethylene glycol, acetone, methanol, isopropanol, glycerines or combinations thereof. According to certain embodiments, the ratio of the amount of organic solvent to the amount of quats may be in a range from about 1:2 to about 1:4 by weight or about 1:3 by weight. According to an embodiment, the one or more quats may be dried under a vacuum. Suitable sources of heat for heating the one or more quats may include a variety of sources known to those skilled in the art. According to one embodiment, the urea may be heated by light such as emitted by heating lamps.

According to an embodiment, the step of drying the urea comprises drying the urea until the urea comprises water in an amount no more than 10% by weight of the urea, or no more than 5% by weight of the urea, or no more than 1% by weight of the urea. According to an embodiment, the step of drying the one or more quats comprises drying the one or more quats until the one or more quats comprises water in an amount no more than 3% by weight of the one or more quats, or no more than 0.5% by weight of the one or more quats, no more than 0.2% by weight of the one or more quats.

The step of combining the one or more quats and urea may comprise essentially any method known in the art. In a particular embodiment, the method comprises spraying the one or more quats onto or over the urea and then mixing the one or more quats into the urea. As a result of the high temperatures and low percentage of water in the one or more quats and urea, the quats may be quickly absorbed in the urea to create a paste. In an embodiment of this invention, the one or more quats may be added to the urea gradually while mixing with the urea or by adding one portion of the one or more quats after another to the urea while mixing the quats into the urea after each portion of the one ore more quats is added to the urea. In a certain embodiment, after the one or more quats have been combined with the urea, the composition may be further dried so as to remove any solvents present in the composition. According to a particular embodiment, the one or more quats and urea are mixed substantially homogeneously throughout the biocide composition.

According to a particular embodiment, the method of obtaining the composition may further include granulating the composition. The step of granulating the quat and urea biocide composition may comprise essentially any method known in the art. In a particular embodiment, the biocide composition is granulated by forcing the composition through a screen.

In accordance with a certain embodiment of the present invention, the quat/urea biocide composition may be packaged in a substantially water vapor impermeable packaging so that the biocide composition stays dry and stable until used. Examples of suitable water vapor barrier packaging such as metal foils and polymer laminates are well known. One such embodiment, for example comprises a co-extruded polyolefin and EVOH laminate.

The composition and/or method of obtaining the biocide may have a substantial effect on the properties of the resulting composition. The composition and/or method may cause the urea and the one or more quats to bind into a single product, the urea to become chelated, and/or the one or more quats to become encapsulated in the urea. Although the exact mechanism by which this enhances the composition is unknown, it is believed that the treatment may (1) increase the stability and shelf-life of the biocide; (2) increase the temperature stability of the biocide; (3) increase the pH range in which the biocide is stable; (4) increase the stability of the biocide in the presence of organic matter; (5) increase the ability of the biocide to reduce surface tension in aqueous environments; and/or (6) leave a film on a treated surface for residual biocidal effect. In a particular embodiment, the biocide may be stored in stable condition for up to five years in a dry state or up to one year while dissolved in a liquid.

According to an embodiment, the quat/urea biocide may be added to water to form an aqueous solution. The amount of the quat/urea biocide present in the aqueous solution may vary depending on the intended application, but generally is present in the aqueous solution in an amount from about 0.001 to about 2% by weight of the aqueous solution or about 0.01 to about 2% by weight of the aqueous solution, or about 0.1 to about 2% by weight of the aqueous solution, or about 0.5 to about 1% by weight of the aqueous solution. According to an embodiment, an aqueous solution comprising the quat/urea biocide may have a surface tension which is less than about 90% of the surface tension of water, or less than about 75% that of water, or less than about 60% that of water or less than about 56% that of water. In other words, according to an embodiment, an aqueous solution comprising the quat/urea biocide may have a surface tension less than about 65 dynes/cm$^2$, less than about 54 dynes/cm$^2$, less than about 42 dynes/cm$^2$, or less than about 40 dynes/cm$^2$. According to an embodiment, an aqueous solution of the quat/urea biocide may have a surface tension from about 39 to about 64 dynes/cm$^2$, or from about 39 to about 54 dynes/cm$^2$, or from about 39 to about 42 dynes/cm$^2$.

Table 1 below presents a correlation between concentration of a quat/urea biocide in aqueous solution to surface tension of the solution and between concentration of quats in the aqueous solution to surface tension of the solution. The quat/urea biocide used to generate the data in Table 1 comprised 60% by weight urea and 40% by weight quaternary ammonium compounds in which 60% of the alkyl chains are $C_{14}H_{29}$, 30% of the alkyl chains are $C_{16}H_{33}$, 5% of the alkyl chains are $C_{12}H_{25}$, and 5% of the alkyl chains are $C_{18}H_{37}$.

TABLE 1

| PPM Quats | Concentration % by weight quat/urea biocide | Surface Tension Dynes/cm2 | % of Reduction |
|---|---|---|---|
| 0 | Water | 71.7 | 0.00 |
| 4 | 0.001 | 64 | 10.74 |
| 40 | 0.01 | 53.5 | 25.38 |
| 400 | 0.1 | 42 | 41.42 |
| 2000 | 0.5 | 40 | 44.21 |
| 4000 | 1 | 39 | 45.61 |
| 8000 | 2 | 40.5 | 43.51 |

According to embodiments of this invention, the proportions of the one or more quats and the urea in the biocide composition and the drying and mixing parameters of the quat/urea biocide and the amount of quat/urea biocide added to water to form an aqueous solution are balanced such that the surface tension of the aqueous biocide solution is sufficiently less than that of water so that the aqueous biocide solution is very dispersible on surfaces of articles to be treated with the aqueous biocide solution. These factors may vary within the ranges described herein to achieve the desirable balance when quats having different alkyl chain lengths are used.

According to an embodiment, the quat/urea biocide may be stable at pH levels in the range from about 3 to 11 and at temperatures of from about −3° C. to about 100° C., or from about 15° C. to about 100° C., or from about 15° C. to about 80° C., or from about 60° C. to about 80° C.

General Biocidal Treatment

According to embodiments of this invention, quat/urea compositions may be used to disinfect a variety of articles or environments. The concentration and frequency of application may vary from one application to another. A drawback of quats, however, is that they are not stable in the presence of heat, and even at temperatures below 50° C., tend to break down and lose their biocidal properties.

Thus, according to an embodiment of this invention, a method for treating an area with a biocide comprises applying a quat/urea biocide as described hereinabove to an article or environment. According to a certain embodiment the method of applying the biocide may comprise applying the quat/urea biocide in an aqueous solution such as is described hereinabove. In particular embodiments, the quat/urea biocide is heat resistant and is stable at higher temperatures and, therefore, the method may include applying the quat/urea biocide at application temperatures up to about 100° C., or from about 15° C. to about 100° C., or from about 40° C. to about 100° C., or from about 60° C. to about 100° C., or from about 80° C. to about 100° C. Therefore, according to particular embodiments, the one or more quats are present in the aqueous solution in a concentration in a range of about 0.3 ppm to about 20000 ppm, or about 1 ppm to about 10000 ppm, or about 4 ppm to about 8000 ppm, or about 40 ppm to about 8000 ppm, or about 400 ppm to about 8000 ppm, or about 2000 ppm to about 4000 ppm. According to embodiments of this invention, methods of applying the biocide include but are not limited to immersion, spraying, fogging, drenching, or fumigation with an aqueous solution of the biocide or distributing the biocide in dry particulate form.

Method of Treating Chicken Carcasses with the Biocide Composition

Generally described, chickens may be processed in an automated system while hanging from shackles on a conveyor. In particular, the shackled birds may be stunned, slaughtered, bled, scalded to loosen the feathers, plucked, eviscerated, chilled, and then removed from the conveyor for butchering and packaging.

Unfortunately, the hot scalding may open pores on the skin and loosen the flesh so as to allow pathogens to penetrate the carcass. Furthermore, the chilling may close the pores and tighten the flesh so as to trap the pathogens within the carcass. It therefore would be desirable to provide a method of treating pathogens in chicken carcasses at the high temperatures of the scalding and in the small crevices within the carcass. The methods may be inexpensive, may require low levels of non-toxic biocide, and/or may provide effective treatment of carcasses in the presence of high levels of organic material.

It has now been discovered that the quat/urea biocide compositions of the present application may be used during the processing of chicken carcasses. Due to the method of obtaining the biocide, the biocide may effectively treat pathogens in the presence of high levels of organic contamination, at high temperatures, and/or in a variety of difficult to reach locations. Furthermore, the method of treating the carcasses may remove pathogens from the chickens, prevent spoilage of the chicken carcasses, and extend the shelf life of the processed chicken.

The method may include the step of applying a hot aqueous biocide solution to a chicken carcass, the hot aqueous biocide solution comprising a quat/urea biocide as described hereinabove and scalding water. According to embodiments of this invention, the biocide composition may comprise urea and quaternary ammonium as described above, and the biocide composition may be obtained using the methods described above. According to embodiments, the scalding water may have a temperature from about 40 to about 80° C. Surprisingly, despite that fact that the biocide composition comprises quaternary ammonium, it may remain stable in the hot scalding water. Furthermore, the quat/urea biocide may reduce the surface tension of the hot scalding water as explained hereinabove so as to penetrate the pores and crevices of the chicken carcass.

According to particular embodiments, the quat/urea biocide composition is present in the hot aqueous biocide solution in an amount from about 0.0025 to about 0.3% by weight of the aqueous solution or about 0.01 to about 0.3% by weight of the aqueous solution, or about 0.0625 to about 0.125% by weight of the aqueous solution, or about 0.0125 to about 0.05% by weight of the aqueous solution or in an amount of about 0.025% by weight of the aqueous solution. Therefore, according to particular embodiments, the one or more quats are present in the aqueous solution in a concentration in a range of about 10 ppm to about 1200 ppm, or about 25 ppm to about 500 ppm, or about 50 ppm to about 200 ppm, or in an amount of about 100 ppm.

The application of the hot aqueous biocide solution may clean the carcass and loosen the feathers, and the biocide in the hot biocide aqueous solution may destroy the pathogen on the carcass. The step of applying the hot aqueous biocide solution may comprise spraying or blasting the hot aqueous biocide solution onto the chicken carcass. Alternatively, the step of applying the hot aqueous biocide solution may comprise immersing the chicken carcass into the hot aqueous biocide solution.

In a particular embodiment, the step of applying the hot aqueous biocide solution comprises immersing the chicken carcass into the solution while suspended from a conveyor. The conveyor may move the carcass through the solution, and a pump may move the solution in a direction that is countercurrent to the movement of the carcass.

According to particular embodiments, the temperature of the hot aqueous biocide solution when applied to the chicken carcasses is in a range of about 40° C. to about 80° C., or about 50° C. to about 80° C., or about 60° C. to about 70° C., or is about 65° C. Furthermore, the pH of the mixture may be in a range of about 3 to about 11, and/or hardness of the water may be up to about 850 ppm $CaCO_3$ or up to about 550 ppm $CaCO_3$.

According to a certain embodiment of this invention, a method for disinfecting chicken carcasses comprises applying an aqueous solution of the quat/urea biocide comprising quats in an amount of about 800 ppm to a poultry slaughter plant environment by fogging the environment once or twice per day, applying an aqueous solution of the quat/urea biocide comprising quats in an amount of about 200 ppm to food contact surfaces such as grinders, mixers, blenders, choppers, piping conveyers, tables, workstations, tanks, tubs, barrels, tote boxes, smoke sticks, hooks, and the like, by spraying or immersion, applying an aqueous solution of the quat/urea biocide comprising quats in an amount of about 400 ppm to non-food contact surfaces such as walls, columns, floors, ceiling light fixtures, ducts, sinks, trash barrels, drums, non-processing machinery, and the like, by spraying or immersion, applying an aqueous solution of the quat/urea biocide comprising quats in an amount of about 400 ppm to boots, gloves, uniforms, and the like, by spraying or immersion, scalding chicken carcasses with a hot aqueous solution of the quat/urea biocide at a temperature of about 65° C. comprising quats in an amount of about 15 ppm, washing the chicken carcasses after further the chicken with a hot aqueous solution of the quat/urea biocide at a temperature of about 65° C. comprising quats in an amount of 50 ppm, chilling the poultry carcasses in an aqueous solution of the quat/urea biocide comprising quats in an amount of about 50 ppm, storing the chicken carcasses in cooled rooms disinfected with an aqueous solution of the quat/urea biocide comprising quats in an amount of about 800 ppm, and shipping the disinfected packaged chicken carcasses in transportation vehicles disinfected by an aqueous solution of the quat/urea biocide comprising quats in an amount of about 400 ppm by spraying such vehicles.

Methods of applying the quat/urea biocide to chicken carcasses in chicken slaughter plants according to certain embodiments of the present invention are set forth in Table 2. The application information in Table 2 is for a quat/urea biocide comprising 60% by weight urea and 40% by weight quaternary ammonium compounds in which 60% of the alkyl chains are $C_{14}H_{29}$, 30% of the alkyl chains are $C_{16}H_{33}$, 5% of the alkyl chains are $C_{12}H_{25}$, and 5% of the alkyl chains are $C_{18}H_{37}$. The quat/urea biocide is mixed with water and applied as an aqueous solution. Concentration means amount of quat/urea biocide in the aqueous solution in grams per liter.

TABLE 2

| USE | DOSE | APPLICATION | NOTE |
| --- | --- | --- | --- |
| Disinfection of areas | 2 g/L | fogging | approximately 8 cc/m$^3$ |
| Disinfection of equipment and surfaces | 1 g/L | spray | approximately 1 liter of solution for 15 square meters |
| Disinfection of boots by immersion | 1 g/L | direct to the water | change solution each third day |
| Disinfection of pre-chillers | 1 g/16 liters of water | direct application | 7,000 to 10,000 birds per 1000 liters |
| Disinfection of chiller | 1 g/16 liters of water | direct application | 7,000 to 10,000 birds per 1000 liters |
| Disinfection of worker's hands | 1/gL | spray or direct application | do not dry hands with towels |
| Disinfection of baskets and transportation vehicles | 1 g/L | direct application or spray | 1 liter per 15 cubic meters |

Method of Treating Poultry Eggs with the Biocide Composition

Newly hatched eggs may contain salmonella bacteria. Even those eggs that do not have bacteria inside when the shell is being formed can be exposed to the pathogen when the bird lays the egg.

Thus, according to another embodiment of this invention, a method of treating poultry eggs comprises applying an aqueous solution of quat/urea biocide as described hereinabove to an outer surface of the eggs. The aqueous quat/urea biocide kills microorganism pathogens on the outer surface of the eggs and inside the egg in some embodiments having lower surface tension. According to a certain embodiment, the method comprises applying an aqueous solution of the quat/urea biocide wherein the one or more quats are present in the aqueous solution in an amount from about 100 ppm to about 1200 ppm at a rate of about 1 to about 3 ml of solution per egg. According to other embodiments, the one or more quats are present in the aqueous solution in an amount from about 400 ppm to about 800 ppm at a rate of about 1 to about 3 ml of solution per egg or about 1.5 ml of solution per egg. The eggs may be advantageously treated immediately after collection. According to embodiments of this invention, the aqueous quat/urea biocide solution may be applied to eggs in a variety of ways including but not limited to immersion, spraying, fogging, and fumigating.

Method of Treating Poultry Farms with the Biocide Composition

According to another embodiment of this invention, a method of treating a poultry farm comprises applying an aqueous solution of quat/urea biocide as described hereinabove to a poultry breeding area. According to a certain embodiment, the method comprises applying an aqueous solution of the quat/urea biocide wherein the one or more quats are present in the aqueous solution in an amount from about 100 ppm to about 1200 ppm at a rate of about 1 liter of the aqueous biocide solution per about 4 to about 15 m$^2$ of breeding area. According to other embodiments, the quat/urea biocide is present in the aqueous solution wherein the one or more quats are present in the aqueous solution in an amount from about 400 ppm to about 800 ppm at a rate of about 1 liter of aqueous biocide solution per about 4 to about 15 m$^2$ of breeding area. When poultry is present, the quat/urea biocide is applied at a rate toward the lighter end of the range. In an embodiment wherein the poultry farm comprises a closed breeding house, the aqueous quat/urea biocide solution is applied at a rate from about 6 to about 10 cc per m3 of the closed breeding house or at a rate of about 8 cc per m$^3$ of the closed breeding house. According to a certain embodiment, the quat/urea biocide may be applied about once per day. According to embodiments of this invention, the aqueous quat/urea biocide solution may be applied to the breeding area in a variety of ways including but not limited to spraying, fogging, and fumigating. According to a certain embodiment, the method comprises fogging the breeding area with an aqueous solution of the quat/urea biocide wherein the quat/urea biocide is present in the aqueous solution in an amount of about 800 ppm at a rate of about 1 liter of the aqueous biocide solution per about 4 to about 15 m$^2$ of breeding area for about 5 to about 10 minutes per day.

According to another embodiment, a method of treating a poultry farm may comprise applying an aqueous solution of quat/urea biocide as described hereinabove to a poultry breeding equipment. According to a certain embodiment, the method comprises applying an aqueous solution of the quat/urea biocide wherein the quat/urea biocide is present in the aqueous solution wherein the one or more quats are present in the aqueous solution in an amount from about 100 ppm to about 1200 ppm at a rate of about 1 liter of the aqueous biocide solution per about 4 to about 15 m$^2$ of equipment surface area. According to other embodiments, the quat/urea biocide is present in the aqueous solution wherein the one or more quats are present in the aqueous solution in an amount from about 200 ppm to about 800 ppm at a rate of about 1 liter of aqueous biocide solution per about 4 to about 15 m$^2$ of equipment surface area. According to embodiments of this invention, the aqueous quat/urea biocide solution may be applied to the equipment in a variety of ways including but not limited to spraying, fogging, and fumigating. According to a certain embodiment, the method comprises spraying the equipment surface area with an aqueous solution of the quat/urea biocide wherein the quat/urea biocide is present in the aqueous solution wherein the one or more quats are present in the aqueous solution in an amount of about 400 ppm at a rate of about 1 liter of the aqueous biocide solution per about 4 to about 15 m$^2$ of equipment surface area.

According to another embodiment of this invention, a method of treating a poultry farm may comprise feeding poultry drinking water comprising a quat/urea biocide such as described hereinabove. Such treatment, when applied in appropriate concentrations and frequency is effective to prevent and/or eliminate pathogens without posing a material risk to animals or humans consuming such treated water. According to embodiments of this invention, the amount of quat/urea biocide is present in the drinking water such that the one or more quats are present in the aqueous solution in a range from about 20 to about 75 ppm or about 25 to about 50 ppm. When poultry consumes the quat/urea biocide treated drinking water, the poultry may have less or substantially no presence of pathogens in their fecal matter thereby leading to less such contamination in the poultry environment and/or in food products, such as meat or eggs obtained from such poultry. In some embodiments, such poultry are fed such quat/urea treated drinking water frequently and persistently such as on a substantially daily basis or even more frequently. Feeding poultry drinking water treated with the quat/urea biocide may decrease need for medicating poultry, reduce premature poultry mortality, increase poultry weight, increase poultry food conversion, and keep poultry farm pipes and other equipment clean without corrosion and free of biofilm.

According to certain embodiments, a method of producing meat from poultry comprises feeding poultry drinking water comprising quat/urea biocide as described hereinabove and then slaughtering the poultry.

According to another embodiment of this invention, a method of breeding poultry comprises applying an aqueous solution of a quat/urea biocide as disclosed hereinabove to poultry eggs and then hatching the poultry eggs. The same methods of treatment including concentrations of the biocide apply to treating eggs for hatching as apply to treating eggs for human consumption described hereinabove.

According to another embodiment of this invention, a method of treating a poultry farm comprises applying an aqueous solution of quat/urea biocide as described hereinabove to a poultry breeding area and poultry breeding equipment, applying an aqueous solution of quat/urea biocide as described hereinabove to poultry eggs and then hatching chicks from the treated eggs, and raising the hatched chicks to chickens while feeding them drinking water comprising an aqueous solution of quat/urea biocide as described hereinabove. Optionally, the method may further comprise washing boots of poultry farm workers with an aqueous solution of quat/urea biocide as described hereinabove and/or slaughtering the chickens raised on the poultry farm while cleaning the chicken carcasses with the hot aqueous solution of quat/urea biocide as described hereinabove.

According to a certain embodiment, a method for disinfecting and controlling proliferation of pathogens in a chicken hatchery comprises immersing chicken egg trays in an aqueous solution of the quat/urea biocide composition comprising quats in an amount 400 ppm, spraying, fogging or immersing chicken eggs in an aqueous solution of the quat/urea biocide comprising quats in an amount of about 200-400 ppm, fogging chicken incubator and hatch rooms with an aqueous solution of the quat/urea biocide comprising quats in an amount of 400 ppm, spraying chicken trays with an aqueous solution of quat/urea biocide comprising quats in an amount of 400 ppm, and spraying chicken transportation vehicles with the quat/urea biocide comprising quats in an amount of 400 ppm. Table 3 below provides information according to certain embodiments of the invention for treating chicken hatcheries. The information in Table 3 is for a quat/urea biocide comprising 60% by weight urea and 40% by weight quaternary ammonium compounds in which 60% of the alkyl chains are $C_{14}H_{29}$, 30% of the alkyl chains are $C_{16}H_{33}$, 5% of the alkyl chains are $C_{12}H_{25}$, and 5% of the alkyl chains are $C_{18}H_{37}$. The quat/urea biocide is mixed with water and applied as an aqueous solution. The dose provided describes the grams of quat/urea biocide per liter of aqueous solution.

TABLE 3

| USE | DOSE | APPLICATION | NOTE |
|---|---|---|---|
| Disinfection of eggs | 1 g/L | spray | 150 ml/30 eggs basket |
| Disinfection of areas | 2 g/L | fogging | 8 cc/cubic meter |
| Disinfection of equipment and surfaces | 1 g/L | spray | 1 liter of solution for 15 m² |

A method for breeding chicken according to an embodiment of the present invention comprises applying an aqueous solution of the quat/urea biocide, comprising quats in an amount of 400 ppm to a chicken breeding area by fogging, spraying, or the like, twice per day, applying an aqueous solution of the quat/urea biocide comprising quats in an amount of 400 ppm to tables, tools, machines, feeding dishes, boots, gloves, and uniforms by spraying or immersing, feeding the chicken drinking water comprising the quat/urea biocide in an amount such that quats are present in the drinking water in an amount of about 25 ppm, and applying an aqueous solution of the quat/urea biocide comprising quats in an amount of about 400 ppm to chicken transportation vehicles by spraying or the like.

Methods of application of the quat/urea biocide to poultry breeding areas and systems in accordance with certain embodiments of the present invention are set forth in Table 4. The application information in Table 4 is for a quat/urea biocide comprising 60% by weight urea and 40% by weight quaternary ammonium compounds in which 60% of the alkyl chains are $C_{14}H_{29}$, 30% of the alkyl chains are $C_{16}H_{33}$, 5% of the alkyl chains are $C_{12}H_{25}$, and 5% of the alkyl chains are $C_{18}H_{37}$. The quat/urea biocide is mixed with water and applied as an aqueous solution. Concentration in grams per liter means the amount of quat/urea biocide added to water.

TABLE 4

| USE | DOSE | APPLICATION | NOTE |
|---|---|---|---|
| Sanitation of drinking water | 65 g/1000 | direct to the distribution tanks | approximate consumption per bird is 0.5 grams of TIMSEN per 42 days cycle |
| Disinfection of areas | 2 g/L | fogging | approximately 8 cc/m³ |
| Disinfection of equipment and surfaces | 1 g/L | spray | approximately 1 liter of solution for 15 m² |
| Disinfection of boots by immersion | 1 g/L | direct to the water | change solution each third day |
| Disinfection of houses | 2 g/L | aspersion to surfaces | |

Hand Dip

Pathogens are often spread by human hands and this can cause the spread of illness and can cause contamination of articles and materials handled by human hands such as in food and beverage production and service industries. For example, clean hands are a necessity in restaurants and many restaurant employees and proprietors must frequently wash their hands on the job.

According to an embodiment of this invention, a method for cleaning a human hand comprises applying an aqueous quat/urea biocide solution according to embodiments described hereinabove to the human hand. According to an embodiment, the aqueous biocide solution may have a temperature from about 15° C. to about 40° C., or about 25° C. to about 40° C., or about 35° C. to about 40° C. during the step of applying the biocide solution to the human hand. According to a certain embodiment, the quat/urea biocide may be present in the aqueous solution in an amount from about 0.001 to about 2% by weight of the aqueous solution or about 0.01 to about 2% by weight of the aqueous solution, or about 0.1 to about 2% by weight of the aqueous solution, or about 0.5 to about 1% by weight of the aqueous solution. Therefore, according to particular embodiments, the one or more quats are present in the aqueous solution in a concentration in a range of about 4 ppm to about 8000 ppm, or about 40 ppm to about 8000 ppm, or about 400 ppm to about 8000 ppm, or about 2000 ppm to about 4000 ppm. According to particular embodiments, the step of applying the aqueous biocide may comprise immersion, spraying, rinsing, and the like. The urea present in the biocide may also reduce chapping of a users hands. In a certain embodiment, such as in a food service or handling environment, the frequency of application to the hand may range from once every 15 minutes to once per hour, or once every 30 minutes, or once every 4 hours due to its residual action.

Beverage Dispensers

Beverage dispensing machines generally comprise one or more sources of beverage or beverage components, one or more dispensing nozzles for dispensing the beverage or beverage components, and a system for delivering the beverage or beverage components from the one or more sources of beverage or sources of beverage components to the one or more nozzles. Such a system for delivering the beverage or beverage components may comprise one or more delivery lines or pumps or both. Pathogens such as bacteria may develop in such a dispensing system or nozzles, or both, and cleaning or replacement of such dispensing systems, or components thereof, and/or such nozzles may be required. In some cases, biofilms develop in the dispensing system or nozzles, or both.

Thus, according to another embodiment of this invention, a method for sanitizing a beverage dispensing machine comprises contacting at least a portion of the beverage dispensing machine with an aqueous quat/urea biocide composition such as embodiments described hereinabove. According to a particular embodiment, the method of sanitizing the beverage dispensing machine comprises flushing at least a portion of the dispensing machine with an aqueous quat/urea comprising water and a quat/urea biocide such as in embodiments described hereinabove. According to certain embodiments, the quat/urea biocide may be present in the aqueous biocide in an amount from about from about 0.001 to about 2% by weight of the aqueous solution or about 0.01 to about 2% by weight of the aqueous solution, or about 0.1 to about 2% by weight of the aqueous solution, or about 0.5 to about 1% by weight of the aqueous solution. Therefore, according to particular embodiments, the one or more quats are present in the aqueous solution in a concentration in a range of about 4 ppm to about 8000 ppm, or about 40 ppm to about 8000 ppm, or about 400 ppm to about 8000 ppm, or about 2000 ppm to about 4000 ppm. According to an embodiment, the step of flushing the beverage dispensing machine may include flushing at least a portion of the dispensing machine with the aqueous quat/urea biocide at a temperature from about −3 to about 100° C., or about 15 to about 100° C., or 55 to about 100° C., or 65 to about 100° C., or 80 to about 100° C., or about 80° C. According to still another embodiment, the step of flushing at least a portion of the dispensing system may comprise flushing at least a portion of the delivery system or nozzles or both.

Food Silos

Food such as grain, peanuts, and the like may become contaminated with biocontaminants such as bacteria, mold, fungus, yeast, and the like when stored in silos. Food stored in silos is sometimes exposed to relatively high temperatures which can further propagate the biocontamination and destabilize or render ineffective biocides that would otherwise reduce, eliminate or prevent the biocontamination. As explained hereinabove, biocides that work at such high temperatures are often expensive or unacceptable for use with food. In addition, many biocides are liquid and this creates humidity problems in the silos causing mold and yeast growth and contamination.

Thus, according to an embodiment of this invention, a method for storing food comprises storing food and a quat/urea biocide, as in embodiments described hereinabove, in a silo. According to a particular embodiment the quat/urea is a dry particulate dispersed substantially throughout the food in the silo. According to a certain embodiment, the amount of quat/urea biocide is present in the silo in an amount from 150 to about 300 grams per metric ton the food in the silo or 200 to about 250 grams per metric ton the food in the silo. Additions of the quat/urea biocide to the food in the silo reduces, eliminates and/or prevents biocontamination of the food in the silo to kill fungus in the food, and is applied in dry form so that it attaches to walls and surfaces of the silo. According to certain embodiments, the step of storing the food comprises storing the food and quat/urea biocide at a temperature from about 15 to about 40° C., or about 20 to about 40° C., or about 30 to about 40° C.

Agricultural Products

Agricultural products often suffer from infection from pathogens such as bacteria, mold, and yeast. Treatment of agricultural products with quat/urea may eliminate or prevent fungal or bacterial infection of such products. Concentration of quat/urea biocide, frequency of application to agricultural products, and coordination of biocide treatment and watering of agricultural products may vary depending on type of agricultural product, type and degree of infection, soil, and climate.

Therefore, according to another embodiment of this invention, a method of treating agricultural products comprises applying an aqueous solution of quat/urea biocide as described hereinabove to an agricultural product. According to an embodiment, agricultural products include crops. According to certain embodiments, such agricultural products include vegetables, including but not limited to rice, wheat, cotton, green peas, apples, peaches, citrus (including but no limited to oranges, grapefruits, and limes), onion, garlic, lettuce, tomatoes, melons (including but not limited to watermelons, cantaloupes, honey dew and the like), potatoes, tobacco, pineapples, strawberries, bananas, mangoes, coffee beans, peanuts, and the like, and ornamentals such as flowers, including but not limited to roses, tulips, and marigolds, turf such as grass and other ground cover vegetation.

According to a certain embodiment, the method comprises applying an aqueous solution of the quat/urea biocide to crops in the field as the crops are growing. According to a certain embodiment, the method comprises applying an aqueous solution of the quat/urea biocide, wherein the one of more quats are present in the aqueous solution in an amount from about 100 ppm to about 2000 ppm, at a rate of about 2 gallons of the aqueous biocide solution per about 1000 ft$^2$ of field in which the crops are growing. According to other embodiments, the one or more quats are present in the aqueous solution in an amount from about 400 ppm to about 1600 ppm and the aqueous biocide solution is applied at a rate of about 2 gallons of the aqueous biocide solution per about 1000 ft$^2$ of field in which the crops are growing. This may be repeated once every 7 to 14 days as needed. According to embodiments of this invention, the aqueous quat/urea biocide solution may be applied to crops in a variety of ways including but not limited to spraying dripping and irrigating. According to a certain embodiment, the method further comprises wetting the crops before applying the aqueous solution of the quat/urea biocide and, optionally, wetting the crops again after application of the biocide.

According to a certain embodiment, the method comprises applying an aqueous solution of the quat/urea biocide to crops after they are harvested. According to a certain embodiment, the method comprises applying an aqueous solution of the quat/urea biocide wherein the one of more quats are present in the aqueous solution in an amount from about 100 ppm to about 2000 ppm to the harvested crops. According to other embodiments, the one or more quats are present in the aqueous solution in an amount from about 200 to about 1600 ppm, from about 400 ppm to about 1600 ppm, or from about 200 ppm to about 400 ppm. According to embodiments of this invention, the aqueous quat/urea biocide solution may be applied to harvested crops in a variety of ways including but not limited to immersion, spraying and rinsing. According to embodiments of this invention, the aqueous quat/urea biocide solution completely covers the exterior or skin of the crops for most effective results. According to embodiments of this invention, the quat/urea biocide may be contacted with the harvested crops for a period of at least about 1 minute, or at least about 2 minutes, or from about 1 to about 3 minutes. According to embodiments of this invention, the harvested crops may be rinsed with potable water after treatment with the quat/urea biocide. Treatment of harvested crops in accordance with embodiments of this invention may prevent, reduce, or eliminate bacteria and yeast that can lead to fruit ripening and thereby slow ripening to extend shelf life of the crops. While embodiments of this invention are applicable to many crops, certain embodiments are particularly suited to extending the shelf life of perishable crops including but not limited to bananas, watermelon, pineapple, strawberries, cantaloupes, mangoes, and the like.

Furthermore, according to another embodiment of this invention, a method comprises feeding the aqueous quat/urea biocide solution to plants, crops, or cut flowers to provide systemic treatment of or protection from microorganisms such as, for example, bacteria, viruses, mold, fungus, and the like.

According to another embodiment, the method comprises applying an aqueous solution of the quat/urea biocide to cut flowers after they are harvested. According to a certain embodiment, the method comprises applying an aqueous solution of the quat/urea biocide wherein the one of more quats are present in the aqueous solution in an amount from about 100 ppm to about 2000 ppm to the cut flowers. According to other embodiments, the one or more quats are present in the aqueous solution in an amount from about 400 ppm to about 1600 ppm. According to embodiments of this invention, the aqueous quat/urea biocide solution may be applied to harvested flowers in a variety of ways including but not limited to immersion, spraying and rinsing. According to another embodiment of this invention, a method for cutting flowers comprises treating a cutting instrument with the aqueous quat/urea biocide solution and thereafter cutting the flowers with the cutting instrument.

Furthermore, according to another embodiment of this invention, a method of treating turf comprises applying an aqueous solution of quat/urea biocide as described hereinabove to turf. According to a certain embodiment, the method comprises applying an aqueous solution of the quat/urea biocide wherein the one of more quats are present in the aqueous solution in an amount from about 100 ppm to about 2000 ppm at a rate of about 2 gallons of the aqueous biocide solution per about 1000 ft$^2$ of turf. According to other embodiments, the one or more quats are present in the aqueous solution in an amount from about 400 ppm to about 1600 ppm at a rate of about 2 gallons of the aqueous biocide solution per about 1000 ft$^2$ of turf. This may be repeated once every 7 to 14 days as needed. According to embodiments of this invention, the aqueous quat/urea biocide solution may be applied to turf in a variety of ways including but not limited to spraying and irrigating. According to a certain embodiment, the method further comprises wetting the turf before applying the aqueous solution of the quat/urea biocide and, optionally, wetting the turf again after application of the biocide.

Methods of application to some crops according to certain embodiments of the invention are set forth in Tables 5 and 6. The application information in Tables 5 and 6 is for a quat/urea biocide used comprising 60% by weight urea and 40% by weight quaternary ammonium compounds in which 60% of the alkyl chains are $C_{14}H_{29}$, 30% of the alkyl chains are $C_{16}H_{33}$, 5% of the alkyl chains are $C_{12}H_{25}$, and 5% of the alkyl chains are $C_{18}H_{37}$. The quat/urea biocide is mixed with water and applied as an aqueous solution. Concentration in ppm means amount of quat in the aqueous solution.

TABLE 5

| CROP | PATHOGEN | APPLICATION | grams/hectare | FREQUENCY |
|---|---|---|---|---|
| Rice | *Pyricularia orizae* | By spraying. | 400-600 g/Ha/60 liters of water | Aspersion at 90-105 days, second application 15 days after depending on time (rain) |
| | *Rhizoctonia solani* | By spraying. | | |
| Wheat | *Helminthosporium* sp. | By spraying. Frequency of application depends upon the weather. | 600 g/Ha | 10 days (rain) 20 days (dry) |
| Cotton | *Aspergillus niger* | By spraying. | 600 g/Ha | 10 days |
| | *Rhizocpus nigricans* | | 600 g/Ha | |
| Potatoes | *Rhizoctonia solani* | By immersion of seeds in water. | 0.5 kg/200 L | 8-15 days |
| | | OR aspersion during sowing. | 3.0 kg/1000 L/Ha | 15 days |
| | *Phytophtora infestans* | By spraying. | 2.0 kg/600 L/Ha | |
| | *Alternaria solani* | By spraying. | 2.5 kg/600 L/Ha | |
| | Late blight | By drenching the soil. | 4.0 kg/1000 L/Ha | |
| Green Peas | *Ascochyta* sp. | By spraying. | 600 g/Ha | 10 days |
| Apples | *Botrytis* sp. | By spraying. | 2 g/L 2 liters per tree | 12 days |
| Oranges | *Botrytis* sp. | By spraying. | 2 g/L 2 liters per tree | 12 days |
| | *Colletotrichum-gloeosporcides* | By spraying. | | 12 days |
| Onion and Garlic | *Alternaria porri* | By spraying. | 600 g/Ha | 10 days |
| Lettuce | *Pseudomonas marginalis* | By spraying. | 200 g/200 liters per Ha | 12 days |
| | *Botrytis cinerea* | By spraying. | 400 g/200 liters per Ha | 12 days |

TABLE 6

| Ornamental Crops | Disease | Interval of Appli-cation | Type of Application | Rate (ppm) |
|---|---|---|---|---|
| Carnation (*Dianthus Caryophyllus*) | *Fusarium oxysporum* | 15 days | Drench | 1600 |
| | *Fusarium roseum* | 5 days | Spray | 800 |
| | *Botrytis cinerea* | 8 days | Spray | 200-400 |
| | *Cladosporium Echinulatum* | 8 days | Spray | 400 |
| | *Alternaria* sp. | 8 days | Spray | 800 |
| | *Pythium* sp. | 15 days | Drench | 800 |
| | *Rhizoctonia* sp. | 15 days | Drench | 800 |
| Rose | *Botrytis cinerea* | 8 days | Spray | 200-400 |
| | *Rhizoctonia* sp. | 15 days | Drench | 800 |
| | *Oidium* sp. (powdery mildew) | 4-8 days | Spray | 400 |
| | *Agrobacterium tumefaciens* | 1 time | Drench | 800 |
| | *Pythium* | 15 days | Drench | 800 |
| Chrysanthemum (*Chrysanthemum morifolium*) | *Botrytis cinerea* | 8 days | Spray | 200-400 |
| | *Alternaria* sp. | 8 days | Spray | 600-800 |
| | *Pythium* sp. | 15 days | Drench | 800 |
| | *Pseudomonas cichorii* | 15 days | Spray | 400-600 |
| Baby's Breath (*Gypsophilia paniculata*) | *Botrytis cinerea* | 8 days | Spray | 200-400 |
| | *Agrobacterium tumefaciens* | 1 time | Drench | 800 |
| | *Erwinia carotovara* | 15 days | Drench | 800 |
| Statice (*Limonium* sp.) | *Botrytis cinerea* | 8 days | Spray | 200-400 |
| | *Pythium* sp. | 15 days | Drench | 800 |
| | *Rhizoctonia* sp. | 15 days | Drench | 800 |
| Aster (*Catstephus chinensis*) | *Fusarium roseum* | 8 days | Spray | 800 |
| | *Botrytis cinerea* | 8 days | Spray | 200-400 |
| | *Oidium* sp. (powdery mildew) | 4-8 days | Spray | 400 |
| | *Agrobacterium tumefaciens* | 1 time | Drench | 800 |
| Gerbera (*Gerbera jamesonii*) | *Fusarium roseum* | 8 days | Spray | 800 |
| | *Botrytis cinerea* | 8 days | Spray | 200-400 |
| | *Pythium* sp. | 15 days | Drench | 800 |
| | *Rhizoctonia* sp. | 15 days | Drench | 800 |
| | *Pseudomonas cichorii* | 15 days | Spray | 400-600 |
| | *Xanthomonias* sp. | 15 days | Spray | 400-600 |
| Alstroemeria | *Botrytis cinerea* | 8 days | Spray | 2-400 |
| | *Pythium* sp. | 15 day | Drench | 800 |
| | *Rhizoctonia* sp. | 15 days | Drench | 800 |
| Snapdragon (*Antinhinum majus*) | *Botrytis cinerea* | 8 days | Spray | 200-400 |
| | *Alternaria* sp. | 8 days | Spray | 800 |
| | *Pythium* sp. | 15 days | Drench | 800 |
| | *Rhizoctonia* sp. | 15 days | Drench | 800 |
| *Delphinium* sp. (*Delphinium* sp.) | *Botrytis cinerea* | 8 days | Spray | 200-400 |
| | *Alternaria* sp. | 8 days | Spray | 800 |
| | *Pythium* sp. | 15 days | Drench | 800 |
| | *Rhizoctonia* sp. | 15 days | Drench | 800 |
| Trachelium | *Botrytis cinerea* | 8 days | Spray | 200-400 |
| | *Alternaria* sp. | 8 days | Spray | 800 |
| | *Pythium* sp. | 15 days | Drench | 800 |
| | *Rhizoctonia* sp. | 15 days | Drench | 800 |
| Stacks (*Mathiola* sp.) | *Botrytis cinerea* | 8 days | Spray | 200-400 |
| | *Alternaria* sp. | 8 days | Spray | 800 |
| | *Pythium* sp. | 15 days | Drench | 800 |
| | *Rhizoctonia* sp. | 15 days | Drench | 800 |
| Anthurium (*Anthurium* sp.) | *Xanthomonas campestris* | 15 days | Spray | 400-600 |
| | *Xanthomonas anthuriae* | 7 days | Spray | 400-600 |
| Post-Harvest Cut Flowers | Bacteria, Fungi | 1 time | Immerse stems 1-2 hours | 200 |
| Disinfestation (Floriculture species including those listed above) | Bacteria, Fungi | 1 time | Immerse in solution 30 seconds | 400 |

Treatment of Citrus Greening

Citrus greening, also known as huanglongbing ("HLB") or Yellow Dragon Disease, is a serious citrus disease which greatly reduces production, destroys the economic value of fruit, and can kill trees. HLB has become one of the major threats against citrus worldwide. This bacterial disease has already reduced citrus production in Asia, Africa, the Arabian Peninsula, and Brazil. This systemic bacteria belongs to the Rhizobia family, and it affects the tree at the time of blooming and creates a yellowing effect throughout the foliage. The bacteria also affects the fruit, giving it a bitter flavor, as well as turning the seeds black. Its effect is a fast pathogenic infestation that creates a very dangerous source of cross contamination for the other surrounding trees. This bacteria is responsible for the death of over 6 million trees worldwide over a span of 3 years.

The vector of this bacterium is a fly insect no larger than 2 mm, which feeds on the juice from the crop's vascular system. Numerous trials involving various bactericides have been performed by various organizations, but these trials have so far yielded very poor results. As such, the currently preferred treatment involves the application of insecticides to control the insect or fly which is the carrier. Unfortunately, this increase in the application of insecticides negatively compromises the productivity of the plantations.

According to an embodiment of this invention, a method for treating citrus greening comprises applying an aqueous quat/urea biocide solution having a composition according to embodiments described hereinabove to the plant.

As described in more detail hereinabove, the one or more quats and urea are dried before they are mixed together and the one or more quats and urea are combined in a manner and in a weight ratio so that the urea and the one or more quats may bind into a single product, the urea may become chelated, and/or the one or more quats may become encapsulated in the urea. The dried quat/urea product may then be combined with water and applied to the plant.

The amount and concentration of quat/urea required to treat the plant depends on the citrus variety and severity of bacterial infestation. According to an embodiment of this invention, the quat/urea may be present in a range of about 2 grams to about 2.5 grams of quat/urea per liter of aqueous solution. Therefore, in certain embodiments the biocide may comprise about 800 to about 1000 ppm quat/urea in an aqueous solution.

According to an embodiment of this invention, the quat/urea biocide solution may be applied by spraying the solution on the affected plant. In other embodiments, treatment may be initiated at early stages of manifestation of the pathogen by applying the solution to the soil by drip irrigation. In certain embodiments, the treatment may be applied by drip irrigation of a solution comprising about 800 to about 1000 ppm quat/urea in an aqueous solution to a sandy soil. In other embodiments, the treatment may be applied by drip irrigation of a solution comprising up to about 4 grams of quat/urea per liter of aqueous solution to a soil having a high anthracite and/or bentonite content. Therefore, in certain embodiments the biocide may comprise up to about 1600 ppm quat/urea in an aqueous solution. An electrical reaction test may be performed on the soil to detect the presence of anthracite and bentonite. If anthracite and bentonite are detected, drip irrigation may be used to apply quat/urea biocide solution to the soil at a concentration of about 4 grams of quat/urea per liter of aqueous solution.

If the solution is sprayed on the foliage of the plant, about 350-450 grams of quat/urea may be applied per Hector. The solution may be applied by hand, such as with a pump sprayer, or may be sprayed by an aircraft or other vehicle. If drip irrigation is used, about 450-650 grams of quat/urea may be applied to the soil every 100 meters.

The foregoing method has proven effective at treating the bacteria responsible for citrus greening. Without intending to be bound by a theory, it is believed that the foregoing biocide solution reduces the surface tension of the water up to 56% creating very microscopic drops that are easily absorbed through the pores of the leaves and foliage. It is believed that the lipophilic quat further acts as a surfactant, allowing the biocide to easily penetrate the waxy cuticle of the plant foliage. The present biocide, therefore, rapidly reaches the vascular system. Once in contact with the bacteria, the biocide breaks the cytoplasmatic membrane by electrical shock due to its high cationic charge, which reacts with the anionic charge of the external surface of the membrane. The present biocide solution also contains urea which is essential to help the plant recuperate from the stress created by the pathogen, and neutralizes the negative effect that the bacteria has on the chlorophyll of the plant. Furthermore, by frequent applications of the biocide (for example, at intervals of 30 to 45 days) the biocide solution will make the plant more resistant and immune to the bacteria.

Method of Treating Peanut Processing Facilities with the Biocide Composition

Peanut processing facilities include but are not limited to peanut cleaning and shelling facilities, peanut roasting or boiling facilities, and peanut oil, butter, or meal manufacturing facilities and the like. Such peanut processing facilities may be subject to biological contamination that presents a human health concern. One example is salmonella contamination which can cause serious human illness. Thus, there is a particular need for a method of reducing, preventing, or eliminating such contamination from peanut processing facilities.

Generally described, peanuts may be processed in facilities including but not limited to storage equipment such as: silos and the like; handling equipment such as conveyors and the like; washing equipment such as sprayers, baths and the like; cooking equipment such as roasters, boilers, and the like; and food processing equipment such as shellers, grinders, blenders, mixers and the like.

It has now been discovered that the quat/urea biocide compositions of the present application may be effective to reduce, prevent or eliminate biological contamination of peanut processing facilities and shelled and unshelled peanuts themselves. As explained hereinabove with regard to other applications, due to the method of obtaining the biocide, the biocide may effectively treat pathogens in the presence of high levels of organic contamination, at high temperatures, and/or in a variety of difficult to reach locations. Furthermore, the method of treating peanuts and peanut facilities may remove pathogens from peanuts, peanut hulls, and peanut processing equipment, and/or extend the shelf life of peanuts and peanut products.

The method may include the step of applying a hot aqueous biocide solution to shelled peanuts, unshelled peanuts, peanut hulls, and/or peanut processing equipment, the hot aqueous biocide solution comprising a quat/urea biocide as described hereinabove and water. According to embodiments of this invention, the biocide composition may comprise urea and quaternary ammonium as described above, and the biocide composition may be obtained using the methods described above. According to embodiments, the water may have a temperature from about 15 to about 80° C. or from about 20 to about 40° C. The quat/urea biocide may reduce the surface tension of the water so as to penetrate the pores and crevices of the peanut hulls.

According to particular embodiments, the quat/urea biocide composition is present in the aqueous biocide solution in an amount from about 0.0025 to about 0.3% by weight of the aqueous solution or about 0.01 to about 0.3% by weight of the aqueous solution, or about 0.0625 to about 0.125% by weight of the aqueous solution, or about 0.0125 to about 0.05% by weight of the aqueous solution or in an amount of about 0.025% by weight of the aqueous solution. Therefore, according to particular embodiments, the one or more quats are present in the aqueous solution in a concentration in a range of about 10 ppm to about 1200 ppm, or about 25 ppm to about 500 ppm, or about 50 ppm to about 200 ppm, or in an amount of about 100 ppm. Furthermore, the pH of the mixture may be in a range of about 3 to about 11, and/or hardness of the water may be up to about 850 ppm $CaCO_3$ or up to about 550 ppm $CaCO_3$.

The step of applying the aqueous biocide solution to peanuts may be as described herein with regard to other harvested crops. The step of applying the aqueous biocide solution to peanut processing facilities may be as described herein with regard to chicken or egg handling facilities.

According to a certain embodiment of this invention, a method for disinfecting peanut processing facilities comprises applying an aqueous solution of the quat/urea biocide comprising quats in an amount of about 800 ppm to a peanut processing facility environment by fogging the environment once or twice per day, applying an aqueous solution of the quat/urea biocide comprising quats in an amount of about 200 ppm to food contact surfaces such as grinders, mixers, blenders, choppers, conveyers, tables, workstations, tanks, tubs, barrels, tote boxes, and the like, by spraying or immersion, applying an aqueous solution of the quat/urea biocide comprising quats in an amount of about 400 ppm to non-food contact surfaces such as walls, columns, floors, ceiling light fixtures, ducts, sinks, trash barrels, drums, non-processing machinery, and the like, by spraying or immersion, applying an aqueous solution of the quat/urea biocide comprising quats in an amount of about 400 ppm to boots, gloves, uniforms, and the like, by spraying or immersion, applying an aqueous solution of the quat/urea biocide comprising quats in an amount of about 200 ppm to peanuts, storing processed peanuts or peanut material disinfected with an aqueous solution of the quat/urea biocide comprising quats in an amount of about 800 ppm, and shipping the peanuts or peanut material in transportation vehicles disinfected by an aqueous solution of the quat/urea biocide comprising quats in an amount of about 400 ppm by spraying such vehicles.

Methods of applying the quat/urea biocide to peanut processing facilities according to certain embodiments of the present invention are set forth in Table 7. The application information in Table 7 is for a quat/urea biocide comprising 60% by weight urea and 40% by weight quaternary ammonium compounds in which 60% of the alkyl chains are $C_{14}H_{29}$, 30% of the alkyl chains are $C_{16}H_{33}$, 5% of the alkyl chains are $C_{12}H_{25}$, and 5% of the alkyl chains are $C_{18}H_{37}$. The quat/urea biocide is mixed with water and applied as an aqueous solution. Concentration means amount of quat/urea biocide in the aqueous solution in grams per liter.

TABLE 7

| USE | DOSE | APPLICATION | NOTE |
|---|---|---|---|
| Disinfection of areas | 2 g/L | fogging | approximately 8 cc/m$^3$ |

TABLE 7-continued

| USE | DOSE | APPLICATION | NOTE |
|---|---|---|---|
| Disinfection of dry storage silos | 150-300 g/ metric ton | powder form, 100 micron particle size | apply dry powder to keep low humidity in silo |
| Disinfection of equipment and surfaces | 1 g/L | spray | approximately 1 liter of solution for 15 square meters |
| Disinfection of boots by immersion | 1 g/L | direct to the water | change solution each third day |
| Disinfection of worker's hands | 1 /gL | spray or direct application | do not dry hands with towels |
| Disinfection of storage equipment and transportation vehicles | 1 g/L | direct application or spray | 1 liter per 15 cubic meters |

Oil Well Drilling

When petroleum wells are drilled, engineers add special drilling "muds" for lubricating drill bits. If drilling mud is not used, or if the mud breaks down over time, it must be replaced which causes significant delays in the drilling operations. In any event, as the drilling mud loses effectiveness, it can cause significant additional wear on the drill bit, drill shaft, and other components of the drill apparatus, and can result in the failure of any or all of these components.

A common mud is synthetic glucose. Over time, however, synthetic glucose breaks down. Further, anaerobic bacteria can grow at the bottom of a deep well and has the dual effect of breaking down the glucose and producing carbon dioxide. When the glucose breaks down, stress and wear on the mechanical parts increase. Meanwhile, the production of carbon dioxide, an acid, results in acid corrosion. Therefore, there is a need in the oil industry for a bactericide that does not require oxygen to work and spreads substantially evenly over the drill bit and related components of the drilling apparatus.

According to an embodiment of this invention, an oil well drilling mud comprises an oil well drilling lubricating material, water, and a quat/urea biocide as described hereinabove. The quat/urea biocide may reduce, eliminate, or prevent the presence of bacteria in the oil well drilling mud and prolong the useful life of the drilling mud. Furthermore, the quat/urea biocide of such embodiments may be particularly effective in oil wells because it functions as a biocide in an anaerobic environment.

According to embodiments of this invention, suitable well drilling lubricants include glucose, typically synthetic glucose. In particular embodiments, the well drilling lubricant is present in the well drilling mud in an amount from about 10 to about 25% by weight of the drilling mud.

According to embodiments of this invention, water is present in the well drilling mud in an amount from about 30 to about 50% by weight of the drilling mud. In addition, according to embodiments of this invention, the quat/urea biocide is present in the well drilling mud in an amount from about 0.1 to about 0.5% by weight of the well drilling mud.

According to another embodiment of this invention, a method for lubricating an oil well comprises feeding an oil well drilling mud, such as embodiments described hereinabove, into an oil well. According to a particular embodiment, the method may further comprise drilling the well while the oil well drilling mud comprising the quat/urea biocide is in the well.

Secondary Oil Recovery Treatment

Geologically, petroleum deposits are a complex mixture of components and structures. A petroleum deposit includes petroleum in liquid phase; a wide variety of various organic compounds that are the product of degradation and interaction of organic matter; and other hydrocarbon byproducts of such degradation. The foregoing components exist in solid, liquid and gas phase, and include various organic gases (methane, ethane, propane, etc.) which have the effect of pressurizing the well.

Drilling a well involves determining the likely location of a petroleum deposit; drilling often great distances until the deposit is tapped; installing the equipment necessary to recover the deposit (pipes, valves, etc.) into the well to retrieve the components of the deposit. In a typical well, once the deposit is tapped, the petroleum deposit is under pressure such that the deposit can be readily retrieved.

Secondary oil recovery involves recovering oil from formerly active wells that have "died," that is, wells in which a portion of the crude oil, and the natural gas and other components that typically are found in petroleum wells, and that "pressurized" the well, have been removed. There are numerous well known methods to recover the deposits in such a well. On well known method involves pumping recovery fluid, essentially water, into which various biocides (to prevent growth and build up of microbes) and surfactants have been introduced into the well, then pumping the mixture of fluid and petroleum out of the well and separating the components. The fluid can be reused.

According to another embodiment of this invention, a method of secondary oil recovery comprises feeding a recovery fluid into an oil well and then removing a mixture of the recovery fluid and oil from the oil well. The recovery fluid comprises a quat/urea biocide such as embodiments described herein. The quat/urea biocide reduces, eliminates and/or prevents the presence of biocontaminants in the well. According to an embodiment, the recovery fluid comprises a carrier fluid and a quat/urea biocide. Suitable carrier fluid comprises a liquid such as water or the like. In addition, according to an embodiment, the quat/urea biocide is present in the recovery fluid in an amount such that the one or more quats are present in the recovery fluid in an amount from about 800 ppm to about 1600 ppm.

According to certain embodiments, the method of secondary oil recovery comprises feeding a recovery fluid comprising the quat/urea into an oil well wherein the oil recovery fluid reaches a temperature within the oil well is from about 5 to about 100° C., or from about 20 to about 80° C., or from about 30 to about 50° C.

The relatively low surface tension of some embodiments of this invention may allow the quat/urea biocide to penetrate cracks and crevices in well drilling equipment and to penetrate through a thicker layer of biocontamination that may be present on surfaces of well drilling equipment and materials. Thus, such embodiments may provide more thorough decontamination than biocides having higher surface tension.

Furthermore, the exact components of the recovery fluid may depend on the acidity of the surrounding soil. Because quat is cationic in aqueous solution, the amount of quat/urea biocide in the recovery fluid may need to be adjusted to compensate for any quat that reacts with the soil.

Biofilm Treatment

Conduits such as pipes carry liquids such as water and the like may become contaminated with pathogens such as bacteria, virus, fungus, yeast, mold, algae, and the like. Such microorganisms attach to interior surfaces of conduits through Van der Waals forces. The micro organisms may then start producing thin fibers and extracellular glycocalyx that attract nutrients from the environment and any organic matter in fluid flowing through the conduit. Such microorganisms may multiply and form colonies on the interior surface of the conduit thereby forming what may be referred to as a biofilm. Biofilm may comprise mineral particles, a variety of microorganisms, and a network of slime or glycocalyx that binds the microorganisms and particles together. Portions of biofilm that sloth off at intervals can spread the microorganisms to distant locations within conduits or pipelines connected to the contaminated conduit. Thus, there is a need for controlling, eliminating, or preventing biofilm in conduits.

Thus, according to another embodiment of this invention, a method for controlling, eliminating, or preventing biofilm in a conduit comprising contacting at least a portion of an interior surface of a conduit with an aqueous quat/urea biocide composition such as embodiments described hereinabove. According to a particular embodiment, the method of controlling, preventing, or eliminating biofilm in a conduit comprises flushing at least a portion of the conduit with an aqueous quat/urea composition comprising water a quat/urea biocide such as embodiments described herein above. According to certain embodiments, a quat/urea biocide may be present in the aqueous biocide solution in an amount from about 0.001 to about 2 percent by weight of the aqueous solution or about 0.01 to about 2 percent by weight of the aqueous solution, or about 0.1 to about 2 percent by weight of the aqueous solution, or about 0.5 to about 1 percent by weight of the aqueous solution. Therefore, according to particular embodiments, the one or more quats are present in the aqueous biocide solution in a concentration in a range of about 4 ppm to about 8000 ppm, or about 40 ppm to about 8000 ppm, or about 400 ppm to about 8000 ppm, or about 2000 ppm to about 4000 ppm. According to another embodiment, the step of flushing the conduit may include flushing at least a portion of an interior surface of the conduit with the aqueous quat/urea biocide at a temperature from about −3 to about 100° C., about 15 to about 100° C., or 55 to about 100° C., or 65 to about 100° C., or 80 to about 100° C., about 80° C. According to some embodiments, the quat/urea biocide aqueous solution is able to penetrate biofilm due to the low surface tension of the aqueous solution and destroy contamination sources that are protected by components of the biofilm such as polymers or polysaccharides.

Treatment of Shrimp Farms

Shrimp farms are also subject to infection such as virus, bacteria, fungus, and the like. For example, three types of viruses that infect shrimp farms include baculovirus, parvovirus, and nodavirus. Bacteria which tend to cause problems in shrimp farm include *vibrio* genus, gram negative *bacillus*, mobile, *pseudomonas*, filamentous bacteria of the *leucotrix* genus. Protozoa such as gregarinas and microsporidies also cause problems in shrimp farms. *Rickettsia* are inferior microorganisms that can infect shrimp. Fungi known to attack shrimp farms include atkinsiella, *pythium*, lagaridium, *fusarium*, and sircipidium. Such infections can diminish shrimp production in shrimp farms. Thus, there is a need for shrimp farm pathogen treatment that does not harm shrimp.

According to another embodiment of this invention, a method of treating a shrimp farm comprises applying an aqueous solution quat/urea biocide solution as described herein above to a shrimp breeding area. According to a certain embodiment, the method comprises applying an aqueous solution of a quat/urea biocide, wherein the one or more quats are present in the aqueous solution in an amount from about 100 ppm to about 1200 ppm, at a rate of about 1 liter of the aqueous biocide solution per 4 to about 15 m$^2$ of breeding area or breeding equipment. According to other embodiments, the quat/urea biocide is present in the aqueous solution such that the one or more quats are present in the aqueous solution in an amount from about 400 ppm to about 800 ppm in the aqueous solution and the aqueous solution is applied at a rate of about 1 liter of aqueous biocide solution per about 4 to about 15 m$^2$ of breeding area or equipment area. According to still another embodiment, the method comprises applying an aqueous solution of quat/urea biocide to a soil basin of a shrimp hatchery such that the quat/urea biocide is applied at a rate of about 150 grams to about 300 grams per hectare, or about 232 grams per hectare. According to a certain embodiment, a method of creating a shrimp farm comprises applying an aqueous solution of the quat/urea biocide to the soil basin before the area is seeded with shrimp larvae. According to yet another embodiment, a method of treating a shrimp farm comprises applying an aqueous solution of quat/urea biocide that is described hereinabove to a basin liner, such as a polymer liner, the quat/urea biocide solution comprising one or more quats in an amount from about 100 ppm to about 1200 ppm, or from about 400 ppm to about 800 ppm, and applied at a rate of about 1 liter of aqueous biocide solution per 4 to about 15 m$^2$. According to still another embodiment, a method of treating a shrimp farm comprises applying an aqueous solution of quat/urea biocide as described hereinabove to water in a shrimp hatchery at a rate of about 75 to about 200 grams per hectare, or about 100 to about 150 grams per hectare, or 118 to 145 grams per hectare. According to a particular embodiment, shrimp eggs or larvae are added to the shrimp hatchery at least 24 hours after treatment of the hatchery with the quat/urea biocide solution.

According to particular embodiments of the invention, treatment of shrimp farms may comprise application of the above described quat/urea biocide to discarded shrimp larvae, cool rooms, employee hands, worker foot baths, equipment such as containers, hoses, nets, tanks, pipes, filters, and the like, drains, feed preparation utensils such as knives, tables, mixers and pelletizers, and shrimp transport vehicles by applying to such areas an aqueous solution of quat/urea biocide comprising one or more quats in an amount from about 100 ppm to about 1200 ppm, or about 400 ppm to about 800 ppm, and applied at a rate of about 1 liter of aqueous biocide solution per 4 to 15 m$^2$ of area. According to particular embodiments, such applications can be implemented by immersion, spraying, rinsing, fogging, and the like. Disinfection of tanks, piping systems, filters, and the like, in accordance with certain embodiments, comprises contacting such items with the quat/urea biocide aqueous solution, without rinsing, and allowing the solution to contact the treated area for at least about 24 hours then allowing the treated area to dry for about five days.

Methods of application to shrimp farms according to certain embodiments of the invention are set forth in Table 8. The application information in Table 8 is for a quat/urea biocide used comprising 60% by weight urea and 40% by weight quaternary ammonium compounds in which 60% of the alkyl chains are $C_{14}H_{29}$, 30% of the alkyl chains are $C_{16}H_{33}$, 5% of the alkyl chains are $C_{12}H_{25}$, and 5% of the alkyl chains are $C_{18}H_{37}$. The quat/urea biocide is mixed with water and applied as an aqueous solution. Concentration in ppm means amount of quat in aqueous solution.

TABLE 8

| USE | DOSE | APPLICATION | NOTE |
|---|---|---|---|
| Disposal of discarded larvae | 1 g/L = 3.8 g/gal | 400 ppm | By Spray or immersion or by fogging or aspersion. |
| Disinfection of cool rooms | 2 g/L = 7.6 g/gal | 800 ppm | Perfect coverage of walls, floors, and roofs. |
| Footbath | 1 g/L = 3.8 g/gal | 400 ppm | By Spray or immersion |
| Disinfection of equipment (containers, hoses, nets, etc.) | 1 g/L = 3.8 g/gal | 400 ppm | By Spray 1 liter of solution for 15 m². |
| Disinfection of areas | 2 g/L = 7.6 g/gal | 800 ppm | Spray or fogging |
| Disinfection of hands | 1 g/L = 3.8 g/gal | 400 ppm | By Spray or immersion. Apply solution in direct contact with skin without posterior rinse. |
| Disinfection of all tanks, piping system, filters and all other gadgets | 1 g/L = 3.8 g/gal | 400 ppm | by immersing in TIMSEN solution for at least 24 hours, and, without rinsing, allowed to dry for about 5 days. It may be necessary to do this routine after every 2 cycles. |
| Washing of feed preparation equipment (knives, tables, mixers, pelletizers, etc.) | 1 g/L = 3.8 g/gal | 400 ppm | Utensils must be immersed in a recipient that contains a disinfectant solution and allow a contact of five minutes, let it dry, it is necessary to wash. By immersion |
| Drains | 2 g/L = 7.6 g/gal | 800 ppm | spray |
| Transport Vehicles | 2 g/L = 7.6 g/gal | 800 ppm | Spray or fogging |

Treatment of Fish Tanks

Fish tanks are subject to infection such as virus, bacteria, fungus, and the like. According to another embodiment of this invention, a method of treating a fish tank comprises applying an aqueous solution quat/urea biocide solution as described herein above to the fish tank. According to a certain embodiment, the method comprises applying an aqueous solution of a quat/urea biocide, wherein the one or more quats are present in the aqueous solution in an amount from about 100 ppm to about 1200 ppm, or about 400 ppm, to the fish tank before fish are added and then rinsing the tank. According to another embodiment, the method comprises applying an aqueous solution of a quat/urea biocide to live fish in a tank, wherein the one or more quats are present in the aqueous solution in an amount from about 0.5 ppm to about 1 ppm. According to some embodiments for live fish, the live fish may be treated with the aqueous solution for about 1 hour on each of 3 consecutive days or on alternate days for 6 days.

Pulp and Paper

Microorganisms such as bacteria, fungi, and algae are typical contaminants in fabrication of paper. When recycled paper is used to make paper, there may be even more contamination because some recycled paper material is further contaminated with microorganisms. Microorganisms may cause serious problems during pulp handling, paper making and converting operations. Thus, there is a need to control, reduce, or eliminate microorganisms from paper pulp and paper such that one may produce a better quality product, reduce the number of rejected number of products, reduce the number of loses, reduce loss time and/or save machinery costs.

Thus, according to another embodiment of this invention, a method for making paper comprises adding to paper pulp a quat/urea biocide such as that described hereinabove. According to a certain embodiment, the method comprises applying the quat/urea biocide to paper pulp in an amount wherein the one or more quats are present in the paper pulp in an amount from about 1 ppm to about 100 ppm, or about 10 ppm to about 75 ppm, or about 15 ppm to about 50 ppm, or about 25 ppm. According to a certain embodiment, a method for making paper comprises adding to paper pulp a quat urea biocide, wherein the temperature of the paper pulp is from about 10 to about 60° C., or about 15 to about 45° C.

According to another embodiment of this invention, a method of disinfecting paper manufacturing equipment comprises applying to the paper manufacturing equipment an aqueous solution of a quat/urea biocide as described hereinabove. According to a certain embodiment, the method comprises applying an aqueous solution of the quat/urea biocide wherein the one or more quats are present in the aqueous solution in an amount from about 100 ppm to about 1200 ppm at a rate of about 1 liter of the aqueous biocide solution to about 4 to about 15 m² of equipment area. According to still another embodiment of the present invention, the step of applying the aqueous quat/urea biocide solution comprises applying solution to the paper making equipment.

Animal Wash

Animals may carry illness and/or odor causing pathogens on their hair and/or skin and may spread those pathogens to other animals and humans. Soaps and shampoos may be inadequate to kill such pathogens or protect the animal from subsequent infection. Thus, there is a need for a method for controlling pathogen infection on animals and the spread of such pathogens.

According to an embodiment of this invention, a method for controlling pathogens on an animal comprises applying an aqueous quat/urea biocide solution having a composition according to embodiments described hereinabove to the skin or hair of the animal or both. According to an embodiment, the aqueous biocide solution may have a temperature from about 15° C. to about 40° C., or about 25° C. to about 40° C., or about 35° C. to about 40° C. during the step of applying the biocide solution to the animal. According to a certain embodiment, the quat/urea biocide may be present in the aqueous solution in an amount from about 0.001 to about 2% by weight of the aqueous solution or about 0.01 to about 2% by weight of the aqueous solution, or about 0.1 to about 2% by weight of the aqueous solution, or about 0.5 to about 1% by weight of the aqueous solution. Therefore, according to particular embodiments, the one or more quats are present in the aqueous solution in a concentration in a range of about 4 ppm to about 8000 ppm, or about 40 ppm to about 8000 ppm, or about 400 ppm to about 8000 ppm, or about 2000 ppm to about 4000 ppm. According to particular embodiments, the step of applying the aqueous biocide may comprise immersion, spraying, rinsing, drenching, and the like. The urea present in the biocide may also reduce chapping of the animal's skin. In a certain embodiment, the frequency of application to the animal may range from once every week, or once every month, or once every 3 months due to its residual action. According to a certain embodiment, the method for a method for controlling pathogens on an animal comprises washing the animal with a cleanser, such as soap or shampoo or the like, and thereafter applying an aqueous quat/urea biocide solution having a composition according to embodiments described hereinabove to the skin or hair of the animal or both. This method may be applied to a variety of animals including, but not limited to livestock, such as cows, horses, pigs, sheep, and the like, and pets, such as dogs and cats and the like. According to certain embodiments, the aqueous biocide solution may be effective to treat fungus and eczema of the skin and feathers and/or may make animal coats or feathers shiny and healthy. Furthermore, according to certain embodiments, the aqueous biocide solution may be effective to control sweat odor and reduce exposure to fleas, flies, and other insects.

According to a certain embodiment, a method for sanitizing cow udders is provided and comprises applying an aqueous quat/urea biocide solution having a composition according to embodiments described hereinabove to the cow udder. This treatment may be effective to prevent mastitis. According to an embodiment, the aqueous biocide solution may have a temperature from about 15° C. to about 40° C., or about 25° C. to about 40° C., or about 35° C. to about 40° C. during the step of applying the biocide solution to the animal. According to a certain embodiment, the quat/urea biocide may be present in the aqueous solution in an amount from about 0.001 to about 2% by weight of the aqueous solution or about 0.01 to about 2% by weight of the aqueous solution, or about 0.1 to about 2% by weight of the aqueous solution, or about 0.5 to about 1% by weight of the aqueous solution. Therefore, according to particular embodiments, the one or more quats are present in the aqueous solution in a concentration in a range of about 4 ppm to about 8000 ppm, or about 40 ppm to about 8000 ppm, or about 400 ppm to about 8000 ppm, or about 2000 ppm to about 4000 ppm. According to particular embodiments, the step of applying the aqueous biocide may comprise immersion, spraying, rinsing, drenching, and the like. The urea present in the biocide may also reduce chapping of the udder. In a certain embodiment, the frequency of application to the udder may range from once every day or once every week due to its residual action.

According to a another embodiment, a method for sanitizing cow milking equipment is provided and comprises applying an aqueous quat/urea biocide solution having a composition according to embodiments described hereinabove to the cow milking equipment. According to an embodiment, the aqueous biocide solution may be applied to the cow milking equipment in the same manner as to the cow udder. Equipment to be treated may include, but is not limited to the rubber milking tips and the milking cans.

According to still another embodiment, a method for sanitizing a dairy plant is provided and comprises applying an aqueous quat/urea biocide solution having a composition according to embodiments described hereinabove to the diary handling equipment. According to an embodiment, the aqueous biocide solution may be applied to dairy equipment including but not limited to pipelines, tanks, valves, and the like to reduce, prevent, or eliminate bacteria, fungus, especially lactus *bacillus*, and other biological contamination. Some bacterial contamination, like lactus *bacillus*, is difficult to control due to formation of calcium stones, called milk stones, in diary processing equipment. Thus, according to a certain embodiment, the aqueous biocide solution may be applied to dairy equipment along with a non-ionic detergent for removing the calcium stones without damaging the equipments surfaces such as the pipe surfaces.

Treatment of Swimming Pools

Swimming pools are also subject to infection such as virus, bacteria, fungus, algae, and the like. Thus, there is a need for swimming pool pathogen treatment that does not harm humans.

According to another embodiment of this invention, a method of treating a swimming pool comprises applying an aqueous solution quat/urea biocide solution as described hereinabove to swimming pool surfaces, water in a swimming pool and/or equipment operatively associated with the swimming pool. According to a certain embodiment, the method comprises applying an aqueous solution of a quat/urea biocide to swimming pool surfaces or swimming pool equipment surfaces, at a rate of about 1 liter of the aqueous biocide solution per 4 to about 15 $m^2$ of swimming pool area or associated equipment area, wherein the one or more quats are present in the aqueous solution in an amount from about 100 ppm to about 1200 ppm, or from about 200 ppm to about 600 ppm, or at about 400 ppm. According to particular embodiments of the invention, treatment of swimming pools may comprise application of the above described quat/urea biocide to equipment such as containers, hoses, nets, tanks, pipes, filters, drains and the like. According to particular embodiments, such applications can be implemented by immersion, spraying, rinsing, fogging, and the like. Disinfection of tanks, piping systems, filters, and the like, in accordance with certain embodiments, comprises contacting such items with the quat/urea biocide aqueous solution, without rinsing, and allowing the solution to contact the treated area for at least about 24 hours then allowing the treated area to dry for about five days.

When using aqueous solution quat/urea biocide solution as described hereinabove to water in a swimming pool in which humans will be swimming, a far lower concentration of the biocide is used. Thus, according to still another embodiment, a method of treating a swimming pool comprises adding the quat/urea biocide as described hereinabove to water in a swimming pool such that the one or more quats are present in aqueous solution in the swimming pool water in an amount from about 1 ppm to about 3 ppm. The pH of the water may range from 3 to 11, but may be less cloudy at more neutral pH.

According to certain embodiments, the quat/urea biocide comprises 60% by weight urea and 40% by weight quaternary ammonium compounds in which 60% of the alkyl chains are $C_{14}H_{29}$, 30% of the alkyl chains are $C_{16}H_{33}$, 5% of the alkyl chains are $C_{12}H_{25}$, and 5% of the alkyl chains are $C_{18}H_{37}$. The quat/urea biocide is mixed with water and applied as an aqueous solution. Concentration in ppm means amount of quat in aqueous solution.

In order to maximize the effectiveness of the treatment, the foregoing biocide solution is preferably applied without blending or mixing the biocide solution with other products. In particular, the biocide solution should not be mixed with anionic products, since the anions would react with cationic components of the solution.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description therein, may suggest themselves to those skilled in the art without departing from the spirit of the present invention and/or the scope of the appended claims

EXAMPLE 1

Making the Biocide Composition

A biocide composition is prepared using a batch process. 400 lbs of alkyl dimethyl benzyl ammonium chlorides in which 60% of the alkyl chains are $C_{14}H_{29}$, 30% of the alkyl chains are $C_{16}H_{33}$, 5% of the alkyl chains are $C_{12}H_{25}$, and 5% of the alkyl chains are $C_{18}H_{37}$ is combined with 100 lbs of ethylene glycol to create a quat mixture. The quat mixture is gradually heated to a temperature of about 50° C. until substantially all water is evaporated from the quat. Separately, 600 lbs of pharmaceutical grade urea is heated to about 100° C. until substantially all water is evaporated from the urea. The heated quat mixture is then sprayed over heated urea and mixed with the urea to form a quat/urea biocide mixture with a paste-like consistency. The quat/urea biocide mixture is dried to remove the solvent and create a biocide composition, and the biocide composition is forced through a screen to granulate the biocide. The quat/urea biocide is then packaged in drums to protect the granules from moisture.

EXAMPLE 2

Treatment of Chicken Carcasses with Biocide Composition

A quat/urea biocide composition prepared using the process described in Example 1 was mixed with water to prepare 9,954 liters of aqueous solution with 200 ppm quat/urea biocide. The quat/urea biocide solution was heated to about 60° C. and placed in a scalding tank, and 2000 chicken carcasses were treated in the tank over a 20 minute period, each carcass having a residence time of about 3 minutes in the tank. The process was then repeated with no biocide in the scalding tank.

After chilling and processing, the chicken carcasses that had been scalded in the tank containing the biocide tested negative for E. Coli and were found to have an average level of fecal coliforms of about 120 nm p/g. The chicken carcasses that had been scalded in the tank without biocide tested positive for E. Coli and were found to have an average level of fecal coliforms of about 944 nm p/g.

Samples of the chicken were then packaged and placed in a refrigerated display. The chicken carcasses that had been scalded in the tank containing the quat/urea biocide had a normal odor and a pink color after 12 days of display. The chicken carcasses that had been scalded without biocide had a pale color and strong odor after 5 days of display, and a brown color and "stench" odor after 7 days of display.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

I claim:

1. A method of making a biocide composition comprising:
    drying urea, and drying at least three quats by heating; and thereafter,
    combining the at least three quats, a chelator, and the urea to form a chelated quat/urea biocide composition, comprising spraying the at least three quats onto the urea,
    wherein the at least three quats are independently represented by the formula

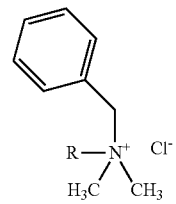

wherein R for the at least three quats is independently an alkyl chain with a length of 8 to 18 carbons;
wherein the drying urea comprises heating the urea to a temperature in a range from about 90 to about 110° C.

2. The method of claim 1, wherein the step of heating the at least three quats comprises gradually heating the at least three quats to a temperature in a range from about 30 to about 40° C.

3. The method of claim 1, wherein the step of heating the at least three quats comprises heating the at least three quats in the presence of a solvent.

4. The method of claim 1, further comprising granulating the biocide composition.

5. The method of claim 1, further comprising adding organic solvent to the at least three quats before the step of heating the at least three quats.

6. The method of claim 1, wherein the at least three quats and urea are present in the chelated quat/urea biocide composition in amounts based on a weight ratio of quats to urea from about 10:90 to about 90:10, or from about 20:80 to about 60:40, or from about 30:70 to about 50:50, or a weight ratio of about 40:60.

7. The method of claim 1, wherein about 50 to about 100% by weight of the three or more quaternary ammonium compounds present in the chelated quat/urea biocide composition comprises an alkyl chain length in the range of about 12 carbons to about 18 carbons.

8. The method of claim 1, wherein about 50 to about 100% by weight of the three or more quaternary ammonium compounds present in the chelated quat/urea biocide composition comprises an alkyl chain length in the range of about 14 carbons to about 16 carbons.

* * * * *